(12) United States Patent
Khadkikar et al.

(10) Patent No.: US 7,421,883 B2
(45) Date of Patent: Sep. 9, 2008

(54) CAPACITIVE VAPOR SENSOR

(75) Inventors: Prasad S. Khadkikar, West Chester, OH (US); Praveen Ramamurthy, Mansfield, OH (US); Bernd D. Zimmermann, Ashland, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 258 days.

(21) Appl. No.: 11/297,752

(22) Filed: Dec. 8, 2005

(65) Prior Publication Data

US 2007/0131021 A1      Jun. 14, 2007

(51) Int. Cl.
*G01N 7/00* (2006.01)
(52) U.S. Cl. ...................................... 73/31.05
(58) Field of Classification Search ............ 73/23.2
See application file for complete search history.

(56) References Cited

U.S. PATENT DOCUMENTS

| | | | | |
|---|---|---|---|---|
| 4,164,868 A | * | 8/1979 | Suntola | 73/335.04 |
| 4,603,372 A | * | 7/1986 | Abadie et al. | 361/286 |
| 4,644,665 A | * | 2/1987 | Naunapper et al. | 34/389 |
| 4,920,451 A | * | 4/1990 | Sakai et al. | 361/286 |
| 5,598,971 A | * | 2/1997 | Winther et al. | 236/44 A |
| 6,495,892 B2 | | 12/2002 | Goodman et al. | |
| 6,742,387 B2 | * | 6/2004 | Hamamoto et al. | 73/335.04 |

* cited by examiner

*Primary Examiner*—Robert R Raevis
(74) *Attorney, Agent, or Firm*—Harness, Dickey & Pierce, PLC

(57) ABSTRACT

A sensor system for detecting the presence of a target analyte. The system comprises a first conductor, a second conductor, and a sensor film. The sensor film is positioned between the first conductor and the second conductor. The sensor film includes a crosslinked siloxane polymer comprising a monomer having a hydrocarbon side group. The sensor film has an absorptive affinity for the target analyte. The electrical capacitance of the sensor system changes upon absorption of the target analyte by the sensor film.

25 Claims, 4 Drawing Sheets

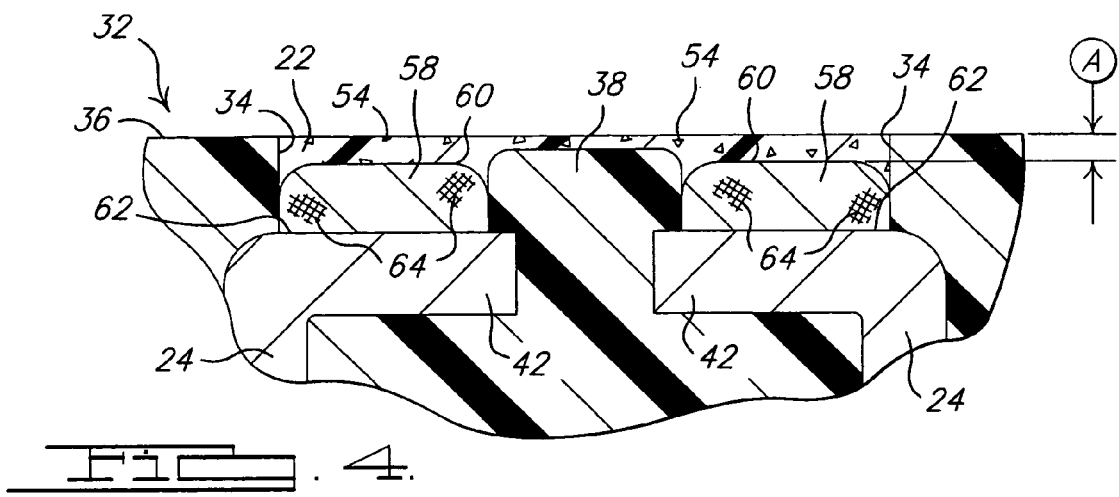
FIG. 4.
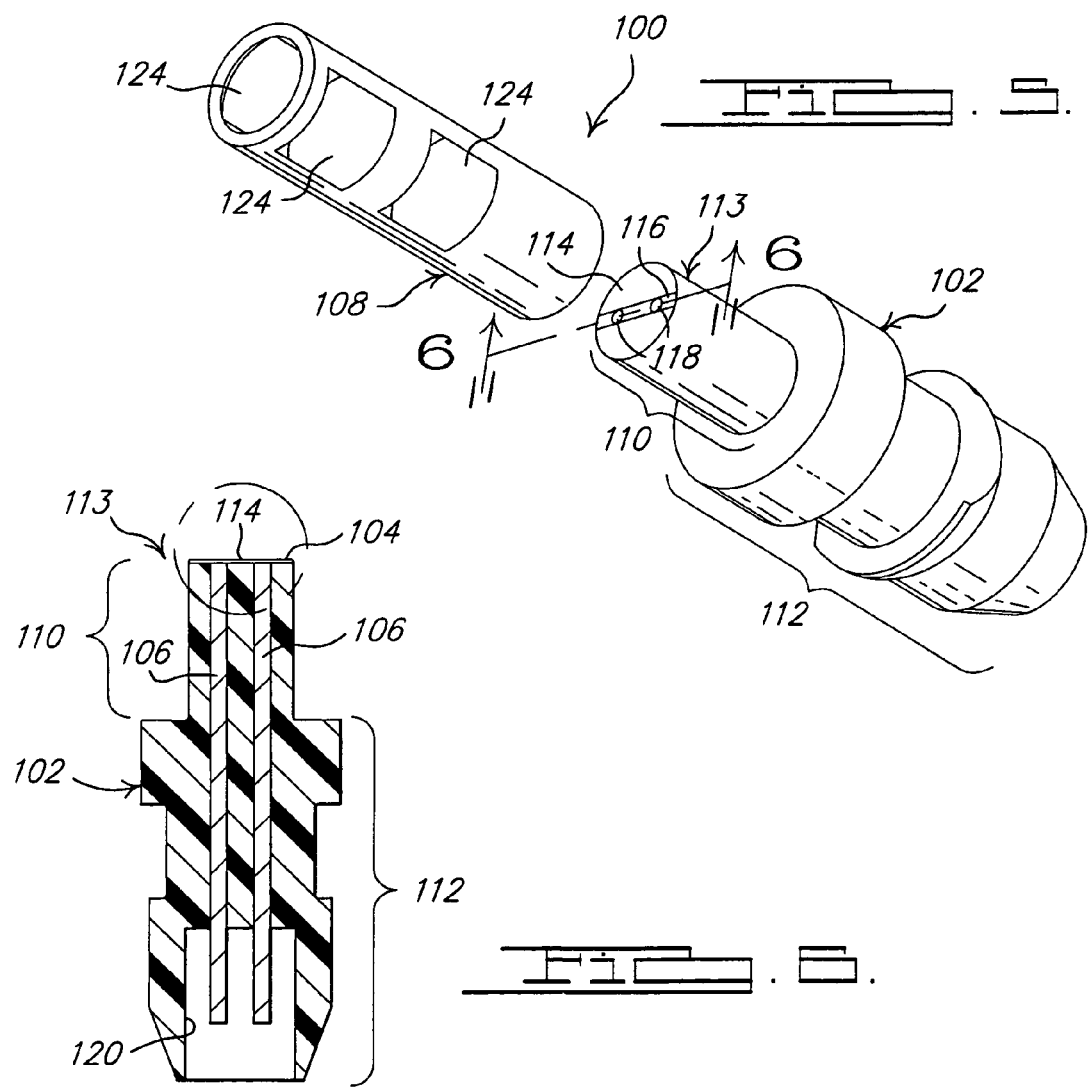
FIG. 5.
FIG. 6.

CAPACITIVE VAPOR SENSOR

FIELD OF THE INVENTION

The present invention relates to vapor sensors. In particular, the present invention relates to a vapor sensor system having a sensor probe that changes capacitance in response to the presence of target analytes.

BACKGROUND OF THE INVENTION

Detecting the presence of specific chemical compounds in the atmosphere is important in a variety of different applications. For example, it is often important to detect the presence and concentration of potentially flammable compounds in the atmosphere. A chemical compound of interest is often referred to as a target analyte.

A variety of different sensor systems known in the art can be used to detect the presence of one or more of the analytes. Most sensor systems employ a sensing component that absorbs the analytes. The sensing component undergoes physical changes upon absorbing one or more of the analytes.

A sensor system typically comprises a sensor probe that includes both the sensing component and a probe body housing (including terminals for transmitting an output). The terminals are typically coupled to a control unit, also part of the sensor system, which analyzes outputs received from the sensor probe. The control unit is coupled to a user interface, typically including an indicating device, which signals when concentration of an analyte exceeds threshold values.

Many sensor systems employ a sensing component that includes a sensor film. The sensor film absorbs the target analytes when they are present. Upon absorption of the analytes, the sensor film undergoes physical changes. Various sensor systems available in the art measure the physical changes in the sensor film to identify the presence of the target analytes.

Such sensor systems may include optical sensor systems, such as fiber optic sensor systems. In fiber optic sensor systems, a beam of light is projected through an optical fiber at a sensor film cladding. Physical changes (e.g. refractive index or color) in the film are monitored. Changes in refractive index occur when analytes are absorbed and change the physical properties of the cladding (including volumetric changes).

Other sensor systems include surface acoustic wave sensor systems (SAWS). In SAWS systems ultrasonic waves are projected through the sensor film between transducers, which detect any modifications in the properties of the sensor film (primarily the mass), translating those changes into the concentration of analyte present.

Another type of sensor system is a conductiometric sensor system, more particularly, a polymer-absorption chemiresistor sensor system. A polymer-absorption chemiresistor sensor system has a polymer sensor film exposed to a surrounding atmosphere. An electrical charge is applied across the polymer film. The polymer absorbs any target analytes that might be present in the atmosphere. Upon absorption of the target analytes, the sensor film undergoes a volumetric change. This change in volume changes the electrical resistance of the sensor film. Conductive particles may be distributed throughout the polymer film to enhance the sensitivity to resistance changes in the material when the volume of the polymer changes.

Each of the above sensor systems typically include a processor or control unit. The processor monitors the physical properties of the sensor film to determine the absence, presence, and concentration of the target analytes. The processor can be coupled to a user interface. The user interface typically includes an indicating device, which generates a signal when the concentration of the target analyte exceeds a predetermined threshold value.

In chemiresistor sensor systems, the resistance of the sensor film changes not only upon the absorption of the analytes, but also in response to changes in ambient temperature. Because detection of target analytes in chemiresistor sensor systems is based on changes in the resistance of the sensor film that occur when the film absorbs target analytes, changes in ambient temperature that change the resistance of the sensor film can negatively affect the sensor system's ability to accurately detect the presence of target analytes. For example, if the sensor film has a positive temperature coefficient of resistance such that the film increases in resistance upon the absorption of target analytes, increases in ambient temperature might cause the sensor system to generate a false signal indicating that target analytes are present when they are not.

While conventional sensor systems perform adequately for their intended uses, they are subject to improvement. Specifically, it would be beneficial to provide a sensor system that: consumes less power as compared to chemiresistor sensors; has an improved sensitivity/response time; and can reliably identify the presence of target analytes regardless of changes in ambient temperature.

SUMMARY OF THE INVENTION

The present invention improves upon the prior art by providing a sensor system that detects the presence or absence of target analytes by measuring changes in capacitance of a probe of the sensor system. Measuring changes in capacitance, as opposed to measuring changes in resistance, is advantageous for a number of reasons, including: 1) a sensor system based on changes in capacitance consumes less power than a sensor system based on changes in resistance; and 2) a sensor system based on changes in capacitance can detect target analytes more quickly than a sensor system based on changes in resistance.

Therefore, the present invention provides an apparatus and method for detecting the presence of a target analyte that comprises measuring an electrical capacitance of a sensor probe. The probe includes a sensor film, which acts as a dielectric, disposed between a first electrode and a second electrode. The sensor film has an absorptive affinity for the target analyte. The capacitance of the probe changes upon absorption of the target analyte by the sensor film. Changes in capacitance of the probe are detected by a control unit. Upon detecting the presence of the target analytes, the control unit transmits an output to a user interface, which provides notification to a user that the target analyte is present.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is a view of a sensing region of the sensor probe of FIG. 3;

FIG. 5 is a perspective view of a sensor probe of FIG. 1 according to an additional embodiment of the present invention;

FIG. 6 is a cross-sectional view of the sensor probe of FIG. 5 taken along line 6-6 of FIG. 5;

DETAILED DESCRIPTION OF THE PREFERRED EMBODIMENTS

The following description of the preferred embodiments is merely exemplary in nature and is in no way intended to limit the invention, its application, or uses.

Figure 1:
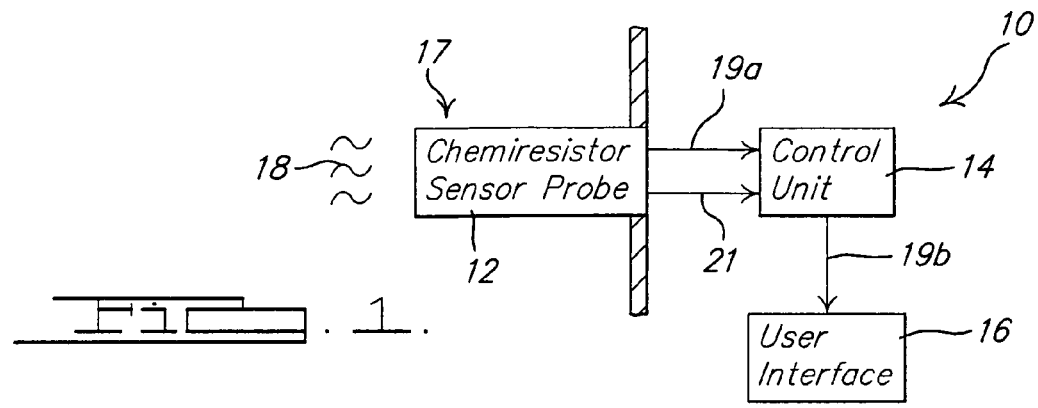
FIG. 1 is a block diagram of a sensor system according to the present invention.

FIG. 1 generally depicts the major components of an exemplary sensor system at 10. The sensor system 10 is generally comprised of a sensor probe 12, a control unit 14, and a user interface 16.

The sensor probe 12 interacts with an external environment 17 to detect the presence of chemical compositions of interest, or target analytes 18. The sensor probe 12 generates a raw output signal 19a based on continuous detection of analytes 18 in the external environment 17. The raw output signal 19a is processed by the control unit 14.

The control unit 14 provides an electrical load and operating commands, both represented by reference numeral 21, to the sensor probe 12. The control unit 14 transmits a calculated output signal 19b to the user interface 16 to relay analysis of the raw output signal 19a from the sensor probe 12. The user interface 16 provides information to an external user about the sensor system 10. The user interface 16 can be of a variety of different forms known in the art and can range from a simple alarm signal to a sophisticated computerized display.

Figure 2:
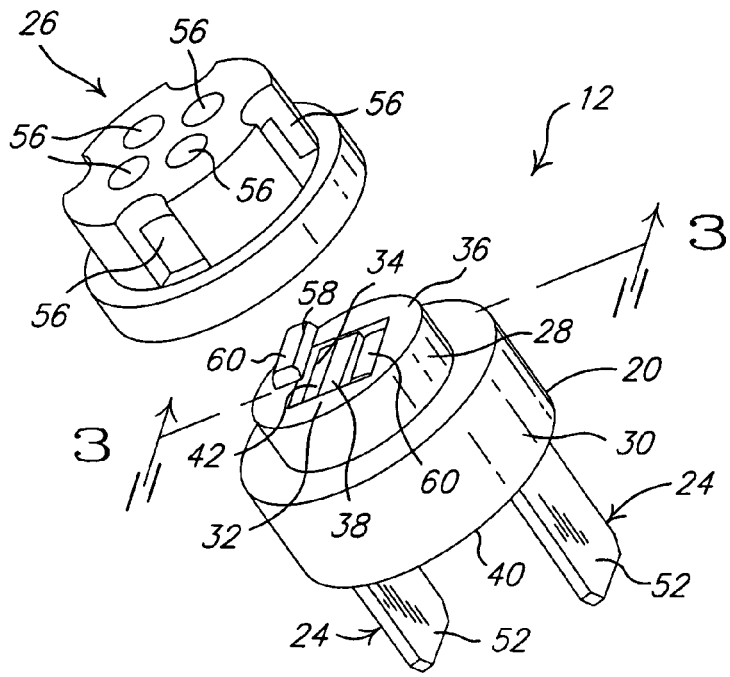
FIG. 2 is a perspective view of a sensor probe of FIG. 1 according to an embodiment of the present invention.

FIG. 2 provides a detailed illustration of the sensor probe 12 according to a first embodiment. The sensor probe 12 generally includes a probe body 20, a conductive sensor element or film 22 (FIG. 4), a pair of terminals 24 extending from the probe body 20, and a protective cap 26.

The probe body 20 includes a first diameter portion 28 and a second diameter portion 30. The first diameter portion 28 has a smaller diameter than the second diameter portion 30. The first diameter portion 28 includes a sensing region 32. The sensing region 32 is comprised of two apertures 34 located within a first control surface 36.

Between the apertures 34 is a second control surface 38. The second control surface 38 extends across the sensing region 32 and is slightly recessed within the first control surface 36.

The terminals 24 are embedded within the probe body 20 and extend from the apertures 34 through both the first diameter portion 28 and the second diameter portion 30. The terminals 24 protrude from the probe body 20 at an underside 40 of the second diameter portion 30. The terminals 24 are made of a conductive material, preferably a metal.

Figure 3:
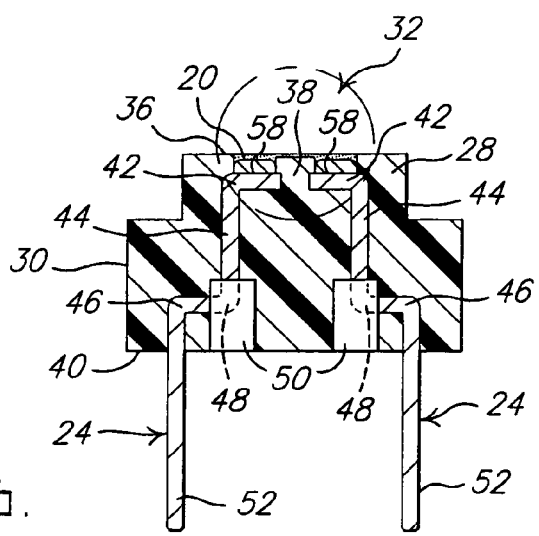
FIG. 3 is a cross-sectional view of the sensor probe of FIG. 2 taken along line 3-3 of FIG. 2.

As seen in FIG. 3, the terminals 24 each comprise a first horizontal portion 42 that is parallel to the first control surface 36 and approximately equals the width of one of the apertures 34. Extending from the first horizontal portion 42 is a first vertical portion 44. The first vertical portion 44 extends through the first diameter portion 28 and into the second diameter portion 30 where the first vertical portion 44 transitions to a second horizontal portion 46.

At the transition point between the first vertical portion 44 and the second horizontal portion 46, the terminals 24 each have an opening 48. The opening 48 receives an alignment rod (not shown) during manufacturing to permit precise alignment of the terminals 24 within the probe body 20. The use of the alignment rod during the molding process results in the formation of a bore 50 within the underside 40 of the probe body 20. The process of manufacturing the probe body 20 is described in detail below.

From the second horizontal portion 46 extends a second vertical portion 52. The second vertical portion 52 extends from the underside 40 of the second diameter portion 30. The second vertical portion 52 extends from the probe body 20 to an appropriate length to permit receipt of the terminals 24 by a corresponding outlet (not shown) that is in communication with the control unit 14.

Illustrated most clearly in FIG. 4, the sensor film 22 is bonded or secured to the sensing region 32 in any suitable manner, such as by solution deposition, so that the sensor film 22 fills the apertures 34 and spans the second control surface 38. The film 22 is in electrical contact with both terminals 24 through either direct or indirect physical contact with the terminals 24.

The sensor film 22 includes a polymer resin that can be any polymer that readily absorbs a target analyte or chemical compound through a gas-solid interface occurring between a surface of the sensor film 22 and the surrounding gas in the external environment 17 (FIG. 1) at a rate that is relatively proportional to the concentration of the analyte in the surrounding gas. Thus, a correlation can be made between the quantity of analyte absorbed and the concentration of the analyte in the surrounding gas. A change in the volume of the sensor film 22 is correlated to the concentration of the analyte present in the gas and is further related to the capacitance of the sensor film 22. Of particular interest are sensor films 22 that detect vaporous hydrocarbon compound analytes, such as one or more volatile organic compounds (VOCs).

The film 22 preferably comprises a crosslinked, polymeric matrix material, but may be any type of sensor film that absorbs one or more different analytes 18 of interest, such as liquids, vapors, or gases. An example of a film 22 that can be used is a crosslinked siloxane polymer comprising a monomer having a hydrocarbon side group with greater than or equal to two carbon atoms, as disclosed in U.S. patent application Ser. No. 10/411,805, filed on Apr. 11, 2003. U.S. patent application Ser. No. 10/411,805 is titled "Vapor Sensor And Materials Therefore" and is assigned to the assignee of the present application, namely Therm-O-Disc, Incorporated. The entire disclosure of U.S. patent application Ser. No. 10/411,805 is incorporated herein by reference. In one preferred embodiment, the film 22 is free of conductive particles. However, in other embodiments the film 22 may include conductive particles 54 positioned throughout the film 22.

The sensing region 32 provides a control over the thickness of the sensor film 22. At its thinnest point, the film 22 is only as thick as the distance between the first control surface 36 and the second control surface 38, represented as distance A in FIG. 4. The thickness of the film 22 may be controlled by varying the distance (distance A) between the first control surface 36 and the second control surface 38. Distance A may be any appropriate distance but is preferably between two and three thousandths of an inch. To control the effective thickness of the film 22 it is important to control the thickness at distance A because the effective thickness of the entire film 22 is primarily dependent upon the thickness of the film 22 at its thinnest point, which is at distance A.

The protective cap 26 may be any suitable cover capable of being inserted. over the first diameter portion 28 of the probe body 20 to protect the sensing region 32 from being disturbed or damaged by foreign materials or objects. The protective cap 26 should be capable of permitting passage of the analytes 18 through the cap 26 for absorption by the film 22. To permit passage of the target analyte 18 through the cap 26, the cap 26 is preferably outfitted with one or more pores or through bores 56. The cap 26 may be secured to the probe body 20 in any suitable manner but is preferably secured using a suitable adhesive.

The robustness of the probe 12 can be increased by providing a strong mechanical bond between the film 22 and the terminals 24. The mechanical bond can be provided by inserting a porous or mesh electrode 58 between the film 22 and the terminals 24. The electrode 58 can be made of any suitably conductive material but is preferably a metal.

As illustrated in FIG. 4, the electrode 58 has an upper surface 60 and a lower surface 62. The upper surface 60 includes a porous or mesh surface 64. The lower surface 62 is in electrical and mechanical contact with the terminals 24 and is secured to the terminals 24 in any suitable manner, such as through sintering.

The upper surface 60 is in electrical and mechanical contact with the film 22. The porous or mesh surface 64 provides the upper surface 60 with a large porous or mesh surface area. The film 22 seeps into the porous or mesh surface area of the upper surface 60 to interlock with the upper surface 60, thus providing a strong mechanical bond between the upper surface 60 and the film 22. By increasing the surface area of the connection between the upper surface 60 and the film 22, the porous or mesh surface 64 increases the number of bonds between the upper surface 60 and the film 22. Use of the electrode 58 extends the life of the sensor probe 12 by preventing separation of the film 22 from the terminals 24 over time as the film 22 expands and contracts in response to absorption of the target analytes 18. Any of the terminals described herein can include the porous or mesh surface 64.

The use of a chemical coupling agent between the terminals 24 and the film 22 also enhances the mechanical and electrical bonds between the film 22 and the terminals 24. The coupling agent may be any appropriate adhesive capable of bonding the film 22 to the terminals 24 while permitting an electrical charge to pass between the terminals 24 and the film 22.

Appropriate coupling agents include monoalkoxy titanate coupling agents, such as isopropyl tri-isostearoyl titanate, isopropyl tri(diocty)phosphate, and isopropyl (4-amino) benzenesulfonyl di(dodecyl) benzenesulfonyl titanate; chelate titanate coupling agents, such as di(dioctyl) pyrophosphate oxoethylene titanate, dimethyacryl oxoethylene, and di(dioctyl)pyrophosphate ethylene titanate; quat titanate and zirconate coupling agents, such as 2-n,N-dimethyl-amino isobutanol adduct of di(dioctyl)pyrophosphate oxoethylene titanate; coordinate titanate and zirconate coupling agents such as tetraisopropyl di(dioctyl) phosphito titanate, tetra (2,2 diallyoxymethyl) butyl, and di(ditridecyl)phosphito zirconate; neoalkoxy titanate coupling agents, such as neopentyl (diallyl)oxy, and tri(dioctyl)pyro-phosphato titanate; cyclo-heteroatom neoalkoxy titanate coupling agents, such as cyclo (dioctyl) pyrophosphato dioctyl titanate; neoalkoxy zirconate coupling agents, such as neopentyl (diallyl)oxy, tri(dioctyl) phosphato zirconate; aluminate coupling agents, such as diisobutyl (oleyl) acetyl aluminate and disopropyl (oleyl) aceto acetyl aluminate; and silane coupling agents, such as allyltriethoxysilane and dimethylethoxysilane.

The manufacturing process of the probe body 20 will now be described in detail. The probe body 20 can be manufactured using any appropriate plastic molding technique, such as insert molding. The molding process may be performed using any suitable molding compound, such as 30% glass reinforced polybutylene terephthalate, sold under the trade name VALOX420 by GE Plastics. The molding compound is dried and inserted into a mold that is pre-fabricated to produce a probe body 20 of a desired shape and size.

The mold is specifically designed to produce the probe body 20 with the second control surface 38 slightly recessed below the first control surface 36. By varying the dimensions of the mold, the distance between the control surfaces 36 and 38 can be altered. As described above, the distance that the second control surface 38 is recessed within the first control surface 36 (distance A in FIG. 3) is equal to the thickness of the film 104 at its thinnest portion. Therefore, the thickness of the film 22 can be controlled by modifying the distance between the first control surface 36 and the second control surface 38.

The terminals 24 are first positioned within the mold. To insure proper positioning of the terminals 24 within the probe body 20, the terminals 24 are each mounted within the mold upon separate rods (not shown) that are received by the opening 48 of the terminals 24. Subsequently, the molding compound is inserted into the mold.

After the molding compound hardens, the terminals 24 become trapped within the probe body 20 and are molded in situ. Because the terminals 24 are mounted upon the rods when the probe body 20 is molded around the terminals 24, the bores 50 are formed in the underside 40 of each probe body 20. Before the film 22 and the optional mechanical and chemical binding agents are applied to the terminals 24, the terminals 24 may be cleaned to enhance their performance.

After the probe body 20 is molded about the terminals 24, and the sensing region 32 is formed as a result of the molding process, optional mechanical binding agents, such as the porous or mesh electrodes 58, can be inserted within each of the apertures 34 upon the second vertical portion 52 of the terminals 24. The porous or mesh electrodes 58 are secured to the terminals 24 in any suitable manner, such as through sintering or welding. Depending upon the depth of the apertures 34 and the thickness of the electrodes 58, it may be necessary to compress the electrodes 58 so that the electrodes 58 do not protrude beyond the first control surface 36 or the second control surface 38.

A chemical bond may also be provided between the sensor film 22 and the terminals 24. The chemical bond may be used in addition to or in place of the mechanical bond. The chemical bond is provided by a chemical coupling agent positioned between the film 22 and the terminals 24. The coupling agent may be any suitable coupling agent capable of creating a chemical bond between the film 22 and the terminals 24, including any one or more of the chemical coupling agents described above.

After the optional mechanical and/or chemical coupling agents are placed over the terminals 24, the sensor film 22 is applied over the first control surface 36 and the second control surface 38 in liquid or paste form. The film 22 is applied in excess such that it completely fills the apertures 34, spans the second control surface 38, and extends beyond the first control surface 36. The excess sensor film 22 is removed so that the film 22 does not extend beyond the first control surface 36. The excess film 22 can be removed in any suitable manner, such as by running a razor blade over the first control surface 36. The film 22 is oven cured to complete the process of installing the seal. The oven curing process is typically performed at 130° C. for eight hours.

After the sensor film 22 is applied, the protective cap 26 is placed over the first diameter portion 28 and is secured to the probe body 20 in any suitable manner.

Figure 7:
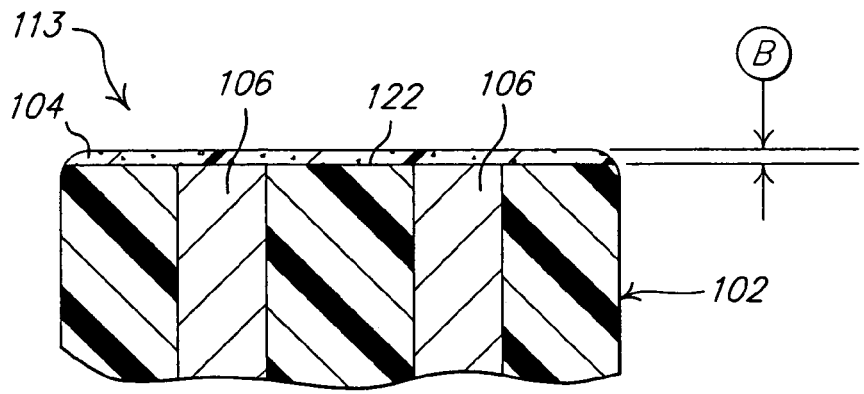
FIG. 7 is a view of the sensing region of the sensor probe of FIG. 6.

An additional embodiment of the probe 12 is illustrated in FIGS. 5 through 7 at 100. Similar to the probe 12, the probe 100 generally includes a probe body 102, a sensor element or film 104 (FIGS. 6 and 7), a pair of terminals 106 (FIG. 5 and 6), and a protective cap 108 (FIG. 5). In one preferred embodiment, the sensor film 104 is free of conductive particles. However, in other embodiments the sensor film 122 can include conductive particles 122 (FIG. 7).

As seen in FIGS. 5 and 6, the probe body 102 includes a neck portion 110 and a base portion 112. The neck portion 110 has a sensing region 113 having a first control surface 114. Recessed within the first control surface 114 is a second control surface 116. The second control surface 116 includes two apertures 118 through which the terminals 106 extend.

The terminals 106 extend from the apertures 118 through both the neck portion 110 and the base portion 112. The terminals 106 terminate in an interior cavity 120 (FIG. 6) of the base portion 112. The interior cavity 120 is sized such that it can receive a corresponding outlet (not shown) of the control unit 14. The outlet engages the portions of the terminals 106 that extend within the cavity 120. The sensor film 104 is placed upon the second control surface 116 such that it spans the apertures 118 and makes electrical contact with the terminals 106. The terminals 106 can include the porous or mesh surface 64 to provide a mechanical bond between the terminals 106 and the sensor film 122.

The first control surface 114 and the second control surface 116 together provide a control over the thickness of the sensor film 104. Specifically, the film 104 is initially applied over the second control surface 116 in excess such that the film 104 extends beyond the first control surface 114. The excess film 104 is subsequently removed so that the film 104 does not extend beyond the first control surface 114. Thus, the thickness of the film 104 is equal to the distance that the second control surface 116 is recessed within the first control surface 114, represented as distance B in FIG. 7. Distance B may be any suitable distance but is preferably between two and three thousandths of an inch.

The protective cap 108 may be any suitable cover capable of being inserted over the neck portion 110 to protect the first control surface 114 and the sensing film 22 from being disturbed or damaged by foreign materials or objects. Similar to the protective cap 26, the protective cap 108 includes one or more pores or through bores 124 that permit passage of the target analytes 18. The cap 108 may be secured to the sensor probe body 102 in any appropriate manner but is preferably secured using a suitable adhesive.

The robustness of the probe 100 can be enhanced by creating a strong mechanical bond between the sensor film 104 and the terminals 106. The mechanical bond is preferably provided by placing a porous or mesh electrode, such as the electrode 58 (FIG. 4), between the film 104 and the terminals 106. The film 104 seeps within the large porous or mesh surface area of the electrode to provide numerous mechanical bonds between the electrode and the film 104. The electrode 58 prevents separation of the film 104 from the terminals 106 over time due to expansion and contraction of the film 104 in response to absorption of the target analytes 18, thereby extending the life of the probe 100.

The robustness of the probe 100 may also be increased by inserting a chemical bond between the terminals 106 and the film 104. The chemical bond may be provided by any chemical coupling agent that is capable of bonding the film 104 to the terminals 106, while at the same time permitting passage of an electrical charge between the terminals 106 and the film 104. Chemical coupling agents that may be used include those listed above in the discussion relating to the sensor probe 12. The chemical bond may be in addition to, or in place of, the mechanical bond provided by the electrode.

The manufacturing process of the probe 100 is substantially similar to the manufacturing process of the probe 12. Therefore, the description of the manufacturing process of the probe 12 equally applies to the probe 100.

Figure 8:
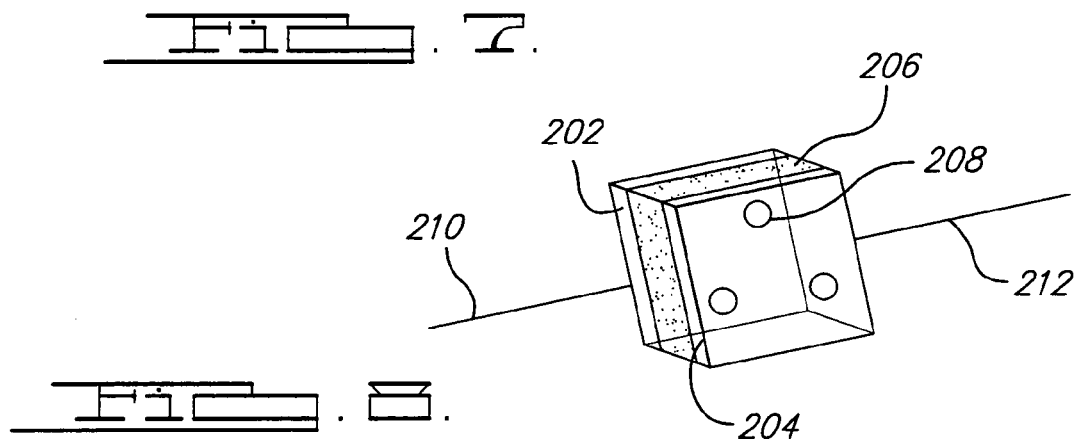
FIG. 8 is a perspective view of a sensor probe of FIG. 1 according to a further embodiment of the present invention.

An additional embodiment of the probe 12 is illustrated in FIG. 8 at reference numeral 200. The probe 200 generally includes a first terminal 202, a second terminal 204, and a sensor element or film 206. The first terminal 202 opposes the second terminal 204. The sensor film 206 is disposed between the first terminal 202 and the second terminal 204. The first and second terminals 202. and 204 can be bonded to the sensor film 206 using a suitable mechanical and/or chemical bond as described above. For example, the terminals 202 and 204 can include the porous or mesh surface 64 to provide a mechanical bond between the terminals 202 and 204 and the sensor film 206.

The first and second terminals 202 and 204 each include apertures 208. The apertures 208 extend. completely through each of the first and second terminals 202 and 204. The apertures 208 provide a passageway for the target analytes 18 through the first and second terminals 202 and 204 to the sensor film 206. The analytes 18 are subsequently absorbed by the sensor film 206.

The first and second terminals 202 and 204 can be any suitable conductive material. For example, the terminals 202 and 204 can be nickel plated copper sheaths. The sides of each terminal 202 and 204 that face the sensor film 206 can include surface features, such as granules, to enhance the bond between the terminals 202 and 204 and the sensor film 206.

The sensor film 206 is the same as the sensor film 22. Therefore, the above description of the sensor film 22 equally applies to the sensor film 206. In one preferred embodiment, the sensor film 206 is free of conductive particles. However, in other embodiments the sensor film 206 can optionally include the conductive particles 54, such as carbon black.

Conductive wires 210 and 212 connect first and second terminals 202 and 204 respectively to the control unit 14.

The probe 200 can be incorporated into a variety of different probe bodies or packages. For example, the probe 200 can be mounted to the body 20 or the body 102. The probe 200 can also be mounted to a substrate, such as a silicon substrate.

Figure 9:
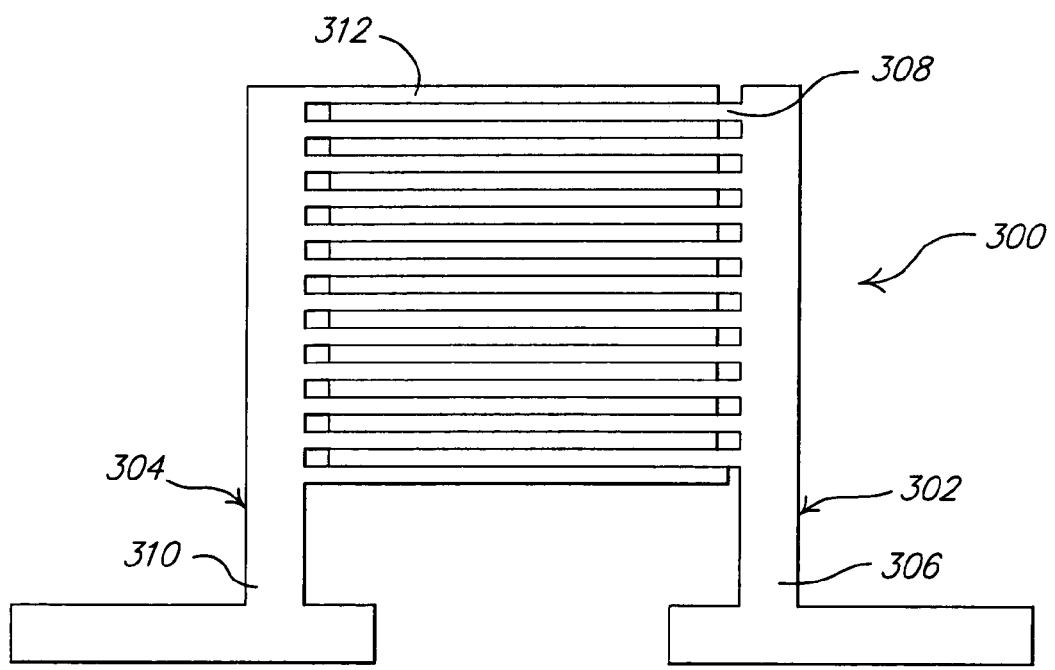
FIG. 9 is a plan view of a sensor probe of FIG. 1 according to a further embodiment of the present invention.

An additional embodiment of the probe 12 is illustrated in FIG. 9 at reference numeral 300. The probe 300 generally includes a first terminal 302 and a second terminal 304. The first terminal 302 includes a first main body 306 and a plurality of first extending portions or fingers 308. The fingers 308 extend from the main body 306 and are spaced apart from each other. Similarly, the second terminal 304 includes a second main body 310 and a plurality of second extending portions or fingers 312. The fingers 312 extend from the main body 310 and are spaced apart from each other.

The first fingers 308 are positioned in the spaces between the second fingers 312 and the second fingers 312 are positioned in the spaces between the first fingers 308. As a result of this arrangement, the first terminals 302 are interdigitated with the second terminals 304. The terminals 302 and 304 can be made of any suitable conductive material, such as the conductive materials used to make the terminals 24 and 202/204 described above.

A sensor film (not shown) is disposed over at least the first and second fingers 308 and 312. The sensor film of this embodiment is the same as the other sensor films described herein, such as the sensor film 22. Therefore, the above description of the sensor film 22 equally applies to the sensor film of this embodiment. The fingers 308 and 312 can include the porous or mesh surface 64 to provide a mechanical bond between the terminals 302 and 304 and the sensor film.

The probe 300 can be mounted to a suitable substrate, such as a ceramic substrate, or can be packaged in any suitable probe body, such as the probe body 20 of FIG. 2 or the probe body 102 of FIG. 5. The interdigitated terminals 302 and 304 can also be included in the probe 200 of FIG. 8 in place of the first terminal 202 and the second terminal 204.

Many advantages are associated with the use of the interdigitated terminals 302 and 304. For example, use of the interdigitated terminals 302 and 304 provides a more accurate measurement of the capacitance of the entire sensor film.

Figure 10:
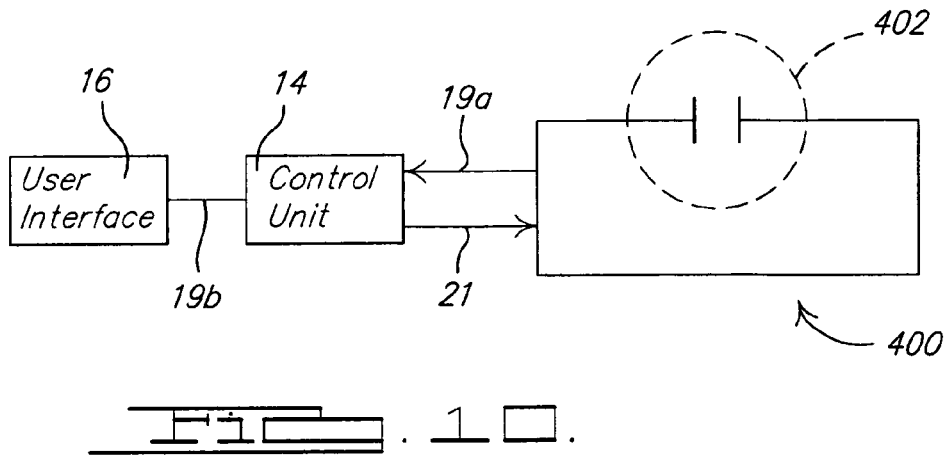
FIG. 10 is a simplified schematic diagram showing circuitry of a sensor probe of the sensor system of FIG. 1.

With additional reference to FIG. 10, a simplified schematic diagram showing the circuitry of each of the sensor probes 12, 100, 200, and 300 is illustrated at 400.

The circuit 400 includes a capacitor 402. The capacitor 402 is comprised of a dielectric sandwiched between two conductive plates. In all embodiments, the dielectric is provided by the sensor film 22, 104, 206. In the embodiment of probe 12, each conductive plate is provided by one of the terminals 24. In the embodiment of the probe 100, each conductive plate is provided by one of the terminals 106. In the embodiment of the probe 200, the conductive plates are provided by the terminals 202 and 204. In the embodiment of the probe 300, the conductive plates are provided by the terminals 302 and 304.

The capacitance of the probe 12, 100, 200, 300 is monitored by the control unit 14. As described in more detail below, the control unit 14 determines whether or not the target analytes 18 are present based on the capacitance of the probe 12, 100, 200, 300. The control unit 14 relays this information to the user interface 16 where the information is displayed to the user.

The operation of the sensor probe 12 will now be described. The operation of the probe 12 is substantially similar to the operation of the probes 100, 200, and 300. Therefore, the description of the operation of the probe 12 also applies to the probes 100, 200, and 300.

The capacitance of the probe 12 is continuously monitored by the control unit 14, which receives signals 19a from the probe 12 representing capacitance. The control unit 14 monitors capacitance using equations known in the art, such as for example $C = \epsilon_0 \epsilon_r (A/d)$. "C" is the capacitance in farads. "$\epsilon_0$" is the permittivity of free space ($8.85 \times 10^{-12}$ F/m). "$\epsilon_r$" is the dielectric constant or relative permittivity of the sensor film 22. "A" is the area of each terminal 24, or electrode 58 when used. "d" is the separation between the terminals 24, or electrodes 58 when used, as measured in meters. Therefore, the capacitance of the probe 12 decreases as the relative permittivity of the sensor film 22 decreases and the distance between the terminals 24 and the electrodes 58 increases.

Upon exposure of the sensor probe 12 to one or more of the target analytes 18 within the external environment 17, the analytes 18 are absorbed by the film 22 causing the film 22 to undergo physical changes depending on the type of the film 22 used. In some embodiments, the film 22 swells upon absorbing the target analytes 18.

As the film 22 absorbs the target analytes 18 and undergoes physical changes, the capacitance of the probe 12 changes. In some embodiments, the change in capacitance is provided by a change in permittivity of the sensor film 22 and/or a change in the distance between the terminals 202 and 204.

Upon detecting this change in capacitance, the control unit 14 transmits a calculated output 19b to the user interface 16 instructing the user interface 16 to alert the user that the target analytes 18 have been detected by the probe 12. The user interface 16 may be any appropriate interface capable of providing an alert to the user. The interface 16 may range in complexity from a simple alarm to a complex computer providing audio and visual alerts.

Figure 11:
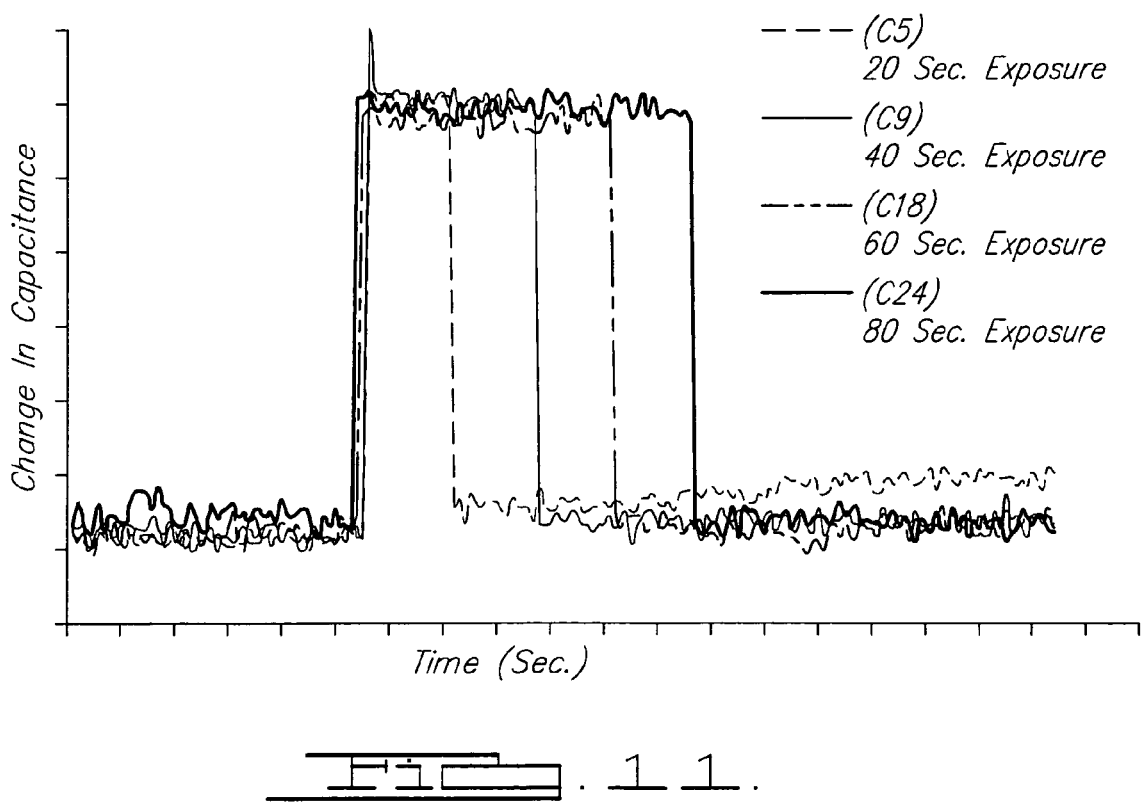
FIG. 11 is a chart illustrating the results of testing performed on four different sensor probes each manufactured according to the probe of FIG. 2.

FIG. 11 illustrates a chart of test results performed on four different sensor probes similar to the sensor probe 12. Each sensor probe includes a sensor material in accordance with the teachings of U.S. patent application Ser. No. 10/411,805. Specifically, the sensor material comprises a crosslinked siloxane polymer having a hydrocarbon side group. In some embodiments the hydrocarbon side group has two or more carbon atoms. In some embodiments, the polymer further includes poly(vinylmethylsiloxane octylmethylsiloxane-dimethylsiloxane).

During the testing, each sensor probe was exposed to the target analytes 18 for different periods of time as indicated. The test results confirm that capacitance of the probe 12 does change, and specifically decrease, when the probes are exposed to the target analyte 18. While the sensor films 22 of each probe used in the testing reported in FIG. 11 did not contain the conductive particles 54, such as carbon black, Applicants have experienced similar test results when the conductive particles 54 are used.

The test results illustrated in FIG. 11 indicate that the capacitance of each probe changes almost instantaneously upon exposure to the analytes 18. As a result, the control unit 14 can quickly detect the presence of the analytes 18 and alert the user by way of the user interface 16. Such rapid detection of the target analyte 18 is particularly important where the analytes are a dangerous substance, such as a flammable vapor.

The test results illustrated in FIG. 11 further indicate that the capacitance of each probe 12 undergoes approximately the same degree of change during the entire time that the target analyte 18 is present. Therefore, there is no ambiguity or gray area in degree of change in capacitance that would make it unclear as to whether the target analyte 18 is present or not.

In order to accurately determine the presence and/or concentration of the target analyte surrounding the probes 12, 100, and 200, the ambient temperature of the external environment 17 must be known and taken into account. Changes in ambient temperature affect both the capacitance and the resistance of the sensor films 22, 104, 206. Specifically, an increase in ambient temperature will decrease capacitance and will increase resistance if the sensor films 22, 104, 206 have a positive coefficient of resistance.

By plotting the resistance against the capacitance across the sensor films 22, 104, 206 at various different temperatures when no analytes 18 is present, it is contemplated that an algorithm can be developed to identify the degree to which such changes in ambient temperature affect both resistance and capacitance. Therefore, the actual resistance and capacitance at different temperatures can be compared to the expected resistance and capacitance using this algorithm to determine if the change in capacitance and resistance is simply due to changes in ambient temperature or the actual presence of the target analytes 18, in which the control unit 14 will notify the user of the presence of the analytes 18 via the interface 16. Knowing whether changes in capacitance and resistance of the sensor films 22, 104, and 206 are due to changes in ambient temperature or due to the presence of the analytes 18 increases the accuracy of the sensor system's ability to detect the analytes 18.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A sensor system for detecting the presence of a target analyte comprising:
    a first conductor;
    a second conductor; and
    a sensor film between said first conductor and said second conductor, said sensor film includes a crosslinked siloxane polymer comprising a monomer having a hydrocarbon side group, said sensor film has an absorptive affinity for the target analyte;
    wherein an electrical capacitance of said sensor system changes upon absorption of the target analyte by said sensor film.

2. The sensor system of claim 1, wherein said hydrocarbon side group includes two carbon atoms.

3. The sensor system of claim 1, wherein said crosslinked siloxane polymer further comprises poly(vinylmethylsiloxane octylmethylsiloxane-dimethlysiloxane).

4. The sensor system of claim 1, further comprising a control unit in receipt of a first output from at least one of said first conductor and said second conductor, said first output indicating a change in the electrical capacitance of said sensor system.

5. The sensor system of claim 4, further comprising a user interface that notifies a user of said sensor system of the presence of said target analyte upon receipt of a second output from said control unit.

6. The sensor system of claim 1, wherein the capacitance of said sensor system decreases upon absorption of the target analyte by said sensor film.

7. The sensor system of claim 1, wherein the capacitance of said sensor system changes to a substantially constant value upon absorption of the target analyte by said sensor film.

8. The sensor system of claim 1, wherein the capacitance of said sensor system changes substantially instantaneously upon absorption of the target analyte by said sensor film.

9. The sensor system of claim 1, wherein said sensor film is at least substantially free of conductive particles.

10. The sensor system of claim 1, wherein said sensor film includes conductive particles.

11. The sensor system of claim 1, wherein said first conductor is a first terminal and said second conductor is a second terminal; and
    wherein said first terminal is interdigitated with said second terminal.

12. The sensor system of claim 1, wherein said first conductor is positioned at a first side of said sensor film and said second conductor is positioned at a second side of said sensor film that is opposite to said first side.

13. The sensor film of claim 1, wherein at least one of said first conductor and said second conductor include a porous surface.

14. A sensor system for detecting the presence of a target analyte comprising:
    a sensor probe that changes in capacitance when the target analyte is present, said sensor probe comprising:
        a first conductor;
        a second conductor; and
        a sensor film between said first conductor and said second conductor, said sensor film having an affinity for the target analyte and including a crosslinked siloxane polymer comprising a monomer having a hydrocarbon side group; and
    a control unit in receipt of an output from at least one of said first conductor and said second conductor, said output represents changes in the capacitance of said sensor probe.

15. The sensor system of claim 14, further comprising a user interface in receipt of said output from said control unit, said user interface notifies a user of said sensor system if the target analyte is present.

16. The sensor system of claim 14, wherein the capacitance of said sensor probe decreases upon absorption of the target analyte by said sensor film.

17. The sensor system of claim 14, wherein the capacitance of said sensor probe changes to a substantially constant value upon absorption of the target analyte by said sensor film.

18. The sensor system of claim 14, wherein the capacitance of said sensor probe changes substantially instantaneously upon absorption of the target analyte by said sensor film.

19. The sensor system of claim 14, wherein said sensor film is at least substantially free of conductive particles.

20. The sensor system of claim 14, wherein said sensor film includes conductive particles.

21. The sensor system of claim 14, wherein said sensor film includes carbon black.

22. The sensor system of claim 14, wherein said first conductor is a first terminal and said second conductor is a second terminal; and
    wherein said first terminal is interdigitated with said second terminal.

23. The sensor system of claim 14, wherein said first conductor is positioned at a first side of said sensor film and said second conductor is positioned at a second side of said sensor film that is opposite to said first side.

24. The sensory system of claim 14, wherein at least one of said first conductor and said second conductor include a porous surface.

25. A method for detecting the presence of a target analyte comprising:
    exposing a sensor probe to an environment that may include a target analyte, the sensor probe having a sensor film comprising a crosslinked siloxane polymer comprising a monomer having a hydrocarbon side group;
    measuring a capacitance of the sensor film;
    detecting a change in the capacitance of the sensor film indicating the presence of the target analyte in the environment;
    generating a signal indicating the presence of the target analyte; and
    conveying the signal indicating the presence of the target analyte to a user.

* * * * *

UNITED STATES PATENT AND TRADEMARK OFFICE
CERTIFICATE OF CORRECTION

PATENT NO. : 7,421,883 B2  Page 1 of 1
APPLICATION NO. : 11/297752
DATED : September 9, 2008
INVENTOR(S) : Prasad S. Khadkikar et al.

It is certified that error appears in the above-identified patent and that said Letters Patent is hereby corrected as shown below:

Column 6,
Line 48, "are-secured" should be --are secured--.

Column 8,
Line 25, "202." should be --202--.
Line 32, "extend." should be --extend--.

Signed and Sealed this

Third Day of March, 2009

JOHN DOLL
*Acting Director of the United States Patent and Trademark Office*